United States Patent [19]
Burch et al.

[11] Patent Number: 6,001,370
[45] Date of Patent: Dec. 14, 1999

[54] ATTENUATED STRAIN OF THE VIRUS CAUSING THE PORCINE REPRODUCTIVE RESPIRATORY SYNDROME (PRRS), AND VACCINES

[75] Inventors: Reina Alemany Burch; Enric Espuna Maso; Pere Riera Pujadas; Narcis Saubi Roca, all of Ciudadania, Spain

[73] Assignee: Laboratorios Hippra, S.A., Spain

[21] Appl. No.: 08/930,330

[22] PCT Filed: Dec. 4, 1996

[86] PCT No.: PCT/ES96/00234

§ 371 Date: Nov. 24, 1997

§ 102(e) Date: Nov. 24, 1997

[87] PCT Pub. No.: WO97/27288

PCT Pub. Date: Jul. 31, 1997

[30] Foreign Application Priority Data

Jan. 25, 1996 [ES] Spain ................................ P 9600168

[51] Int. Cl.$^6$ ........................ A61K 39/12; A61K 39/145; C12N 7/04; C12N 7/08
[52] U.S. Cl. ..................................... 424/204.1; 424/209.1; 424/218.1; 424/815; 424/202.1; 424/201.1; 435/235.1; 435/236; 435/237; 435/239
[58] Field of Search ............................. 424/184.1, 201.1, 424/204.1, 209.1, 218.1, 815, 202.1; 435/235.1, 236, 237, 239

[56] References Cited

U.S. PATENT DOCUMENTS 5,476,778  12/1995  Chladek et al. ...................... 435/235.1

FOREIGN PATENT DOCUMENTS 676467  7/1995  European Pat. Off. .

OTHER PUBLICATIONS

Lager et al, 1995, Second International Symposium on PRRS, Denmark, p. 10 (Abstract Only), Aug. 9, 1995.

G. Labarque, "Efficacy of an American and a European Serotype PRRSV Vaccine After Challenge With American and European Wild–Type Strains of the Virus" P6–C–08, PRRS and Aujeszky's Disease, pp. 251–252.

M. Scortti et al., "Evaluation of the Efficacy of Two Spanish Attenuated–Live Virus Vaccines Against PRRS–Induced Reproductive Disease" P6–P–19, PRRS and Aujeszky's Disease, pp. 291–292.

P.J.G.M. Steverink et al., "Serological Profiles of Pigs Consecutively Challenged With An American and European Strain of the Porcine Reproductive and Respiratory Syndrome Virus" P4–P–08, PRRS and Aujeszky's Disease, pp. 179–180.

Paloma Suarez et al., "Open Reading Frame 5 of Porcine Reproductive and Respiratory Syndrome Virus as a Cause of Virus–Induced Apoptosis" Journal of Virology, vol. 70, May 1996, pp. 2876–2882.

C. Prieto et al., "Transplacental Infection Following Exposure of Gilts to Porcine Reproductive and Respiratory Syndrome Virus at the Onset of Gestation" Veterinary Microbiology, vol. 57, 1997, pp. 301–311.

C. Prieto et al., "Insemination of A Susceptible and Preimmunized Gilts with Boar Semen Containing Porcine Reproductive and Repiratory Syndrome Virus", *Theriogenology*, vol. 47, 1997, pp. 647–654.

C. Prieto et al., Effect of Innoculating Gilts with Porcine Reproductive and Respiratory Syndrome Virus (PRRSV) Near the Time of Conception, Proceedings of the 14th IPVS Congress, Italy, Jul. 7–10, p. 84.

C. Prieto et al., Effect of Inseminating Susceptible and Preimmunized Gilts with Semen Containing Porcine Reproductive and Respiratory Syndrome Virus (PRRSV) Proceedings of the 14th IPVS Congress, Italy, Jul. 7–10, 1996, p. 83.

C. Prieto et al., "Exposure of Gilts in Early Gestation to Porcine Reproductive and Respiratoy Syndrome Virus" *The Veterinary Record*, vol. 138, Jun. 1, 1999, pp. 536–539.

P. Suarez et al., "Direct Detection of the Porcine Reproductive and Respiratory Syndrome (PRRS) Virus by Reverse Polymerase Chain Reaction (RT–PCR)" Archives of Virology, vol. 135, 1994, pp. 89–99.

*Primary Examiner*—Mary E. Mosher
*Assistant Examiner*—Ali R. Salimi
*Attorney, Agent, or Firm*—Rudnick & Wolfe

[57] ABSTRACT

A new attenuated strain (CNCM Institut Pasteur I-1642) of the virus causing the swine disease known as porcine reproductive and respiratory syndrome (PRRS) is described, along with an attenuation and replication procedure of the same by using a new clone obtained from MA-104 monkey kidney cells (CNCM Institut Pasteur I-1643). Because of the innocuousness on swine and the high immunogenic activity, the said new attenuated strain allows the obtaining of vaccines and diagnostic kits which make possible both the early diagnosis of PRRS and an efficient preventive treatment of such disease.

6 Claims, 2 Drawing Sheets

ATTENUATED STRAIN OF THE VIRUS CAUSING THE PORCINE REPRODUCTIVE RESPIRATORY SYNDROME (PRRS), AND VACCINES

This is a rule 371 application based on the priority date of PCT/ES96/00234 filed Dec. 4, 1996.

FIELD OF THE INVENTION

This invention relates to a new attenuated strain of the virus causing the swine disease known as porcine reproductive and respiratory syndrome (PRRS). The attenuation and replication procedure of the virulent strain by using a new cell clone obtained from monkey kidney allows the preparation of vaccines and diagnostic kits that permit the early diagnosis of PRRS and an efficient preventive treatment of such disease.

PRIOR ART

In 1987 it was first detected in North America a swine disease that was defined at that moment as "Mystery Swine Disease" or MSD, and was later known as "Swine Infertility and Respiratory Syndrome", or SIRS. A very similar syndrome was first detected in Central Europe in 1990, and spread later to other European countries, including Spain. At the beginning, in Europe, the disease was named "Porcine Epidemic Abortion and Respiratory Syndrome" or PEARS, and, finally, "Porcine Reproductive and Respiratory Syndrome" or PRRS. This name has become worldwide accepted in reference to the disease.

It is already known that the PRRS etiological agent is a RNA encapsulated small virus, isolated for the first time in The Netherlands, and named as Lelystad virus. It was suggested that this virus belonged to the Arterviridae group. This virus has been described in patent application PCT WO-92/21375 and in European patent EP-B-0587780 (Stichting Centraal Diegeneeskundig Instituut), the latter derived from the former. For the purpose of these applications, an isolate of the above mentioned virus was deposited in the Institut Pasteur of Paris, number I-1102.

The North American type was isolated almost simultaneously with the isolation of the European type virus, as is described in patent application PCT WO-93/03760 (Collins et al.) and European patent application EP-A-0529584 (Boehringer Ing.). For the purpose of these applications, an isolate of the above mentioned virus was deposited in the American Type Culture Collection (ATCC), number VR-2332.

European type and North American type viruses are clearly different, not only in reference to serological reactivity but also relative to the homology degree of nucleotide sequences of significant RNA fragments. In the first two pages of the European patent application EP-A-0676467 (Akzo) there is a detailed description of such differences, with extensive literature citation. In the above mentioned patent application it is concluded that the European type and American type viruses have clearly diverged long time ago. In consequence, it can be expected that eventually effective vaccines against one of these types would be little or no effective at all against the other type.

Different strains have been isolated from both the European and American virus types. Each strain has its own specific characteristics, and several strains have been the object of patent application. For example, patent application PCT WO-93/07898 (Akzo) describes a European strain, and vaccines derived from it, deposited in CNCM (Institut Pasteur), number I-1140. The patent application PCT WO-93/14196 and the European patent application EP-A-541418 (Rhône-Merieux), both derived from the same priority application, describe a new strain isolated in France, deposited in CNCM (Institut Pasteur), number I-1153. The European patent application EP-A-0595436 (Solvay) describes a new American type strain, more virulent than the one initially described, and vaccines thereof. This strain has been deposited in ATCC, but the deposit number is not detailed in the patent application. Finally, Spanish patent application number ES-A-2074950 (Cyanamid Ibérica) describes a so-called "Spanish strain", that is different from other European and American strains. This "Spanish strain" has been deposited in European Animal Cell Culture Collection (EACCC), number V93070108.

In conclusion, it appears evident that the PRRS etiological agent shows a number of varieties, and, in order to fight efficiently the disease, vaccines of different types depending on the viral strain type that infects swine, are needed.

In sows, the disease is characterized by lack of appetite, anorexia, reproductive disorders (abortion, premature parturition, birth of dead or weak piglets, and fetal death, with or without mummification). Sometimes infected sows can die. A less frequent sign is a transient blue color in the ears, abdomen or vulva; for that reason, the disease was first known as "Abortus blauw" in The Netherlands, and "Blue Ear" in United Kingdom. In piglets, these symptoms are age-dependant. In newborn piglets, dyspnea and muscular trembling can be observed, while in older piglets posterior paresia and ataxia is more frequent. In the peak of the outbreak, mortality during first days of age is limited, but can reach 80% in ten day-old piglets. Transiently, infected fattening pigs eat less and show more respiratory problems.

Disease incubation period is very variable, ranging from 5 to 37 days (I. B. Robertson Eurp. Comm. Seminar on PRRS, 11:4–5, Brussels, 1991). Sometimes, the disease spreading is very slow, but, when a farm is affected, the disease can persist several months (B. Thacker, Int. Symp. on SIRS, St. Paul/Minn., 1992).

Antibodies against the virus have been detected by the immunoperoxidase technique (immunoperoxidase monolayer assay, hereinafter IPMA) by day 6 post-infection, as described by Wensvoort G., et al. (The Vet. Quart. 13:121–130, 1991). Antibody titers can reach 1/20,000 five days later, and generally persist for over 12 months. However, some pigs become seronegative 4–5 months later, as reported by V. Ohlinger et al., Meredith, M. De. Pig Dis. Info. Center Cambridge, December 1992. These authors were able to isolate virus after infection from different organs, with a virus titer reaching $10^4$ $TCID_{50}$ (tissue culture infective doses 50%) 6 weeks post-infection in lung, serum, plasma and blood cells homogenates. This indicates that virus and antibodies can persist together several weeks. Moreover, it is well known that animals which survive an outbreak can act as infection source for susceptible pigs. Viremia can be detected from day 1 post-infection, and can last up to 56 days, being usually shorter.

In the hematogenic viral spreading, virus can reach the placenta of pregnant sows. It has been demonstrated that the virus can pass through the placenta and cause fetal death. The maximal fetal susceptibility occurs during last third of gestation. In addition, the virus is able to replicate in fetuses without causing its death. However, the virus has never been isolated from mummified or autolysed fetuses.

In piglets, the disease onset occurs when the level of colostral-acquired maternal antibodies has decreased. Among live-born piglets from infected sows in the last third of pregnancy, some cases of piglets with antibodies against the virus before colostrum lactation have been observed. Usually, these animals show also viremia at birth (C. Terpstra et al. Vet. Q. 13:131–136, 1991).

Despite the destruction of a large number of macrophages, immunosuppressor activity of PRRS-causing virus has not been clearly demonstrated. However, associated secondary infections are frequent, causing severe economical losses in swine farms.

Nowadays, PRRS virus can be found in the majority of countries with an important swine population.

At the present time, PRRS is one of the most important diseases affecting the swine sector due to economic losses, both direct and indirect, caused by secondary agents favored by PRRS virus infection.

The use of inactivated vaccines produced in porcine alveolar macrophage (PAM) cultures gives acceptable results at the laboratory level, but the efficiency in field conditions depends, in part, upon environmental conditions and upon the management of vaccinated animals.

One of the problems that has hindered the obtaining of immunological products against PRRS virus is the limited availability of stable substrates for virus replication.

Until recently, PRRS virus could only be amplified in porcine alveolar macrophage (PAM) cultures (Wensvoort G., et al. in The Vet. Quart. 13:121–130, 1991). The need to use disease-free pigs of a certain age for the obtaining of these macrophages implied several drawbacks. Moreover, susceptibility to viral infection was not guaranteed in the recovered PAM, because cell substrates derived from different animals are always variable. This posed a major drawback in the production of antigen batches of constant and homogenous quality, and each batch needed to be evaluated in order to determine its susceptibility.

For all of these reasons, the reduced availability of stable and continuous cell hosts has hindered severely the study of strategies for the obtaining of mutants based on PRRS virus replication in cell substrates and on selection of attenuated varieties.

One of the main problems to be solved is the need to neutralize the virulent virus avoiding its replication in the PAM, because virus replication causes their destruction.

In consequence, the virus adaptation to a stable substrate derived from a transformed cell line would provide a suitable tool both to obtain attenuated mutants and to prepare inactivated vaccines, thus eliminating the dependence and the variability of the PAM.

Patent application PCT WO94/18311 (Miles) proposes the propagation of a certain PRRS virus strain in an unique clone, designated as clone 9009B, derived from an African green monkey kidney cell line, designated as line MA-104 (M) by the patent applicant, derived in his turn from a commercial cell line known as MA-104. In the patent application it is not stated the deposit of the said unique clone, and therefore the patent execution and reproduction is difficult.

OBJECT OF THE INVENTION

The object of the present invention is a new attenuated strain of PRRS virus that allows to obtain, in a stable and reproducible way, innocuous vaccines for swine with a high efficiency in PRRS prevention.

Another object of the present invention consists in a new cell clone derived from the stable monkey kidney cell line MA-104, capable of supporting PRRS virus growing at higher titers, and of allowing the obtaining of stable viral harvests of the selected attenuated strain, and the obtaining procedure of the said cell clone.

Another object of the present invention are the efficient vaccines against PRRS disease that can be obtained from the new attenuated strain and from mutants thereof, together with the obtaining procedure of the same.

Still another object of the present invention are the diagnostic kits for PRRS disease that can be obtained from the new attenuated strain or from mutants thereof, together with the procedure to obtain the same.

DESCRIPTION OF THE INVENTION

The attenuated strain of PRRS virus object of the present invention derives from the attenuation of a virulent strain isolated from infected pigs in a Spanish farm. In order to fulfill the description adequacy, this attenuated strain has been deposited in the Collection Nationale de Cultures de Microorganismes (CNCM) from Institut Pasteur, with deposit number I-1642. The deposit date is Nov. 23, 1995.

The attenuation of the virulent strain and the replication of the attenuated strain have been done by serial passaging in a cell clone, which is also an object of the present invention, and which was designated as Clon-8 by the authors. This clone derives from a commercial monkey kidney cell line known as MA-104. Also in order to fulfill the description adequacy, a deposit of Clon-8 has been made, in the same above mentioned date, in the CNCM from Institut Pasteur, with deposit number I-1643.

Formerly, the commercial cell line MA-104 was cloned both to select and to isolate Clon-8. This cloning was achieved by suspending cells in an appropriate growing medium (for example Earle's minimum essential medium (Earle's MEM) with fetal bovine serum (FBS)), plating the suspension at different concentrations, selecting and tripsinizing the clones, and expanding them in culture flasks. Clones obtained in this way were cloned successively by using the described techniques until well differentiated clones were obtained.

After discarding clones that showed an irregular behaviour or that were difficult to amplify, the selected clones were tested regarding the infection susceptibility to the starting virulent strain of PRRS virus. Clon-8 was selected due to its high susceptibility for viral strain replication (high $TCID_{50}$) and to the reproducibility and consistency of the viral harvests obtained.

The virulent strain was attenuated by sequencial replication in Clon-8 cultures, preferentially at 34° C. The infectious viral particles contents were determined in order to evaluate the replication viability, and the cytopathic effect (CPE) was examined with the aim to estimate the adaptation degree. According to the results obtained, the virus is able to replicate in Clon-8 without viability loss, at least during 20 passages, and the attained attenuation renders a practically innocuous virus that retains its antigenic activity.

In consequence, PRRS virus attenuated strain object of the present invention is obtained in a stable and industrially reproducible way, thus facilitating its use to obtain both PRRS vaccines and PRRS diagnostic kits.

Comparative tests between pig groups infected either with the virulent strain or the attenuated one show clearly that the attenuated strain is innocuous to animals infected with it. On the other hand, the attenuated strain object of the present invention shows a high replication efficiency in seronegative pigs, and is able to elicit seroconversion in animals inoculated with doses as low as 200 $TCID_{50}$ by intramuscular route. The antibodies elicited in this way persist at least 80 days.

Consequently, the attenuated strain object of the present invention is an excellent basis to prepare vaccines for the preventive treatment of swine against PRRS. Such vaccines can be prepared by using any well-known method by the skilled in the art, and in different conventional forms, such as aqueous dispersions, oil emulsions, liposome compositions, in lyophilized form, etc. Vaccine compositions can be completed with different adjuvants, such as immunostimulants, emulsifiers, stabilizers, etc. Vaccines can be administered by the intramuscular or subcutaneous, intranasal, intratracheal, cutaneous, percutaneous or intracutaneous routes.

Effective vaccine doses can be very variable, ranging in a preferred form between $10^2$ and $10^6$ TCID$_{50}$ of the attenuated strain object of the present invention.

The vaccines obtained, also an object of the present invention, can also be formulated as polyvalent vaccines, together with another live or inactivated porcine virus, or together with live or inactivated bacteria.

As it is obvious for the skilled in the art, vaccines can also be prepared containing viral antigens derived from the viral strain object of the present invention, for example vaccines containing the said strain in a thoroughly inactivated form by using any conventional method, for example thermic or chemical methods, vaccines containing capsule or RNA fragments of said strain, etc.

The attenuated strain object of the present invention can also be used to prepare, by applying conventional techniques, suitable diagnostic kits containing the antigenic elements capable to detect antibodies in seropositive animals. For example, an IPMA procedure for the detection of PRRS antibodies can comprise the following steps:

a) Adaptation of the attenuated virus object of the present invention to a stable cell culture, preferently to Clon-8, in a culture microplate, in such a way that each well is infected with about 20–40 infective particles.

b) Fixation of infected cells to the solid phase with known fixatives.

c) Detection of porcine sera antibodies by incubating them in the microplate, followed by staining of the said antibodies in the microplate by IPMA techniques.

BRIEF DESCRIPTION OF DRAWINGS

Two pages with four drawings are attached to the present description, and are part thereof. In the drawings, the following is represented in an illustrative and non-limiting way.

EXAMPLES

Figure 1:
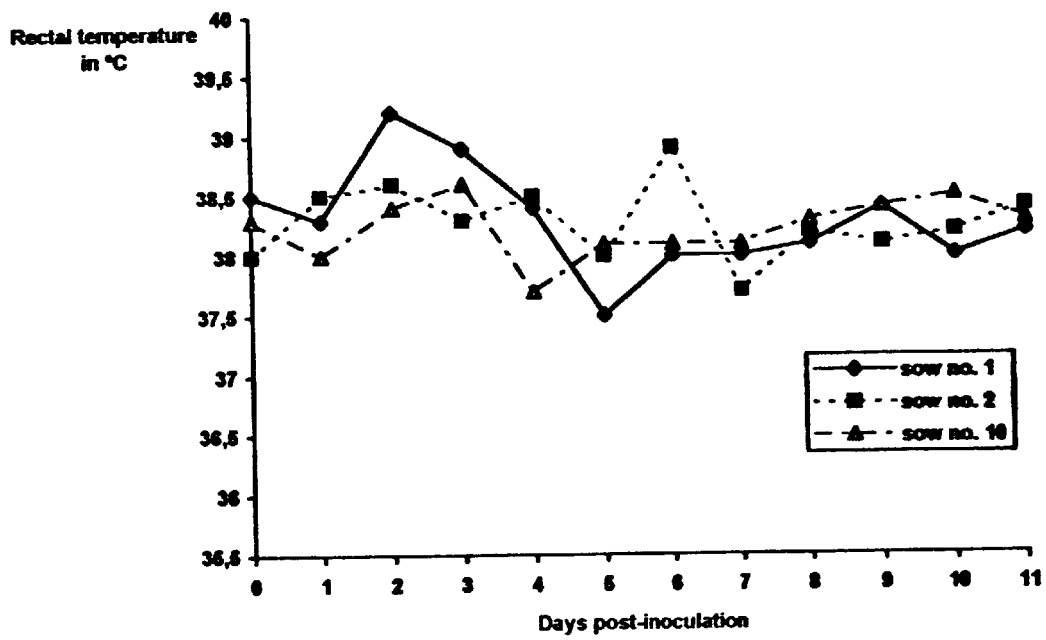
FIG. 1 shows a two-dimension figure representing the rectal temperature evolution in pregnant sows inoculated by intranasal route with the attenuated strain object of the present invention.

Several examples of procedures are shown with the aim to illustrate more accurately the description of the present invention. Such examples should not be considered as scope-limiting.

Example 1

Obtaining of Cell Clones from the Stable Monkey Kidney Cell Line MA-104

Six passages of the selected PRRS virulent strain were done by using the stable monkey kidney cell line MA-104 supplied by the European Animal Cell Culture Collection (EACCC), deposit number 85102918, in static culture cell monolayers grown in plastic culture flasks, in Earle's MEM medium supplemented with 10% Fetal Bovine Serum (FBS), at 37° C. and without $CO_2$ supplement. The viral harvests were collected at 6–7 days post-inoculation in each passage.

In order to study the yield of the viral harvest, the cell line was inoculated with the virulent strain at different multiplicities of infection (hereinafter MOI). The yields obtained of the viral harvest were low (between $10^3$ and $10^4$ TCID$_{50}$/ml), and insufficient to be used in vaccine production, even after four adaptation passages.

In these experiments, it was observed that only part of the infected cells were susceptible to the virulent virus, while the rest of the cells remained refractory to infection. For this reason, this cell line was cloned with the aim to select those cell populations that were totally susceptible to the virulent strain.

Clonal selection was done as follows:

A suspension of the cell line was diluted in Earle's MEM with 20% FBS, and different dilutions were plated in 96 well microplates (NUNC®). Plates were incubated for 8 days at 37° C. in 5% $CO_2$. On day 3, wells that contained only one cell were selected by microscope observation, and trypsinized on day 8. Forty-four clones were obtained in this way. Thereafter, the clones obtained were expanded in culture flasks until a suspension of $5 \times 10^7$ cells/ml was obtained. These cells were subsequently cloned a second and a third time by using the same procedure.

After the third cloning, the 44 obtained clones were expanded until 25 ml of a cell suspension of each clone containing $6 \times 10^7$ cells/ml was obtained. The media used throughout the process contained 20% FBS.

These clones were further selected according to their growing and viability characteristics.

Example 2

Selection of the Cell Clone Clon-8

The clones obtained in the previous example were evaluated according to their growing efficiency, and those that showed amplification problems, irregular morphology or were difficult to maintain at 37° C., were discarded. Thirty-five clones were discarded after this previous selection, and the remaining 9 clones were selected.

The selected cell clones were infected with a suspension of the PRRS virus virulent strain at the eighth viral passage (P-8) in PAM cultures (as described in Bloemberg, M. et al., Vet. Microb. 42, 361–371, 1994). An adaptation process to the cell clones was done previously: virus was replicated at 37° C. during 3 passages by maintaining 80–90% confluent monolayers in contact with the viral suspension during 6 days, then freezing at −80° C. and thawing 24 hours later.

Earle's MEM supplemented with 10% FBS and gentamycin (0.4 mg/ml) was used as infection medium. Neither antifungal nor antiyeast compounds were employed. Each viral harvest obtained in this way was titrated in the corresponding cell clone. After analyzing the results, it was concluded that the 9 clones were susceptible to the viral infection, with titers equal or over $10^{4.2}$ TCID$_{50}$ ml. The results are shown in Table I.

TABLE I

Sensitivity of the obtained cell clones to the selected virulent strain

| CLONE OR CELL LINE | TITER AS $TCID_{50}/ml$ |
|---|---|
| Uncloned cell line | $10^3$ |
| Clone 1 | $10^{5.75}$ |
| Clone 2 | $10^{4.5}$ |
| Clone 3 | $10^{5.2}$ |
| Clone 4 | $10^{5.3}$ |
| Clone 8 | $10^6$ |
| Clone 29 | $10^{5.75}$ |
| Clone 30 | $10^{5.38}$ |
| Clone 41 | $10^{5.38}$ |
| Clone 44 | $10^{4.2}$ |

As can be seen in table I, the uncloned cell line shows a very low virus-sensitivity and, therefore, its use as antigen to obtain effective vaccines seems not feasible. Table I also shows that some clones, especially Clon-8, are more sensitive to the virus than the uncloned cell line. The Clon-8 is particularly noticeable. Titers up to $10^6$ $TCID_{50}/ml$ can be obtained in the viral harvest from Clon-8.

According to the results described above, Clon-8 was selected. Several assays were performed to study the reliability of this clone. In the different assays the titers of the viral harvests were highly reproducible, showing values among $10^5$ and $10^7$ $TCID_{50}/ml$.

Example 3

Obtaining the Attenuated Viral Strain

The attenuated viral strain object of the invention is obtained by replicating at 34° C. the selected virulent strain in Clon-8 cell cultures.

The virus-infected Clon-8 cell monolayers were maintained at 34° C. until CPE was developed. The CPE was always detected between 24 and 48 hours later than in cultures maintained at 37° C. However, no significant differences were found in the CPE features developed at both temperatures.

The resulting viral harvests were titrated by using Clon-8 cell monolayers. Additionally, the identity of the virus was checked by IPMA.

The virus was inoculated to Clon-8 75 cm² cell monolayers near confluence and left to adsorb 2 hours at 34° C. Next, the infection medium was added to the monolayer. The infection medium was Earle's modified Minimal Essential Medium supplemented with 10% FBS and previously warmed up to 34° C.

The 75 cm² flask was placed in a 34° C. incubator and checked daily until a clear CPE was observed. When 80–95% of the cell monolayer showed CPE, usually between the 5th and 7th day post-infection, the viral harvest was collected. The viral harvest was then centrifuged at 2000 rpm and the supernatant was titrated to determine virus titer ($TCID_{50}/ml$).

By using the above described method 20 passages were made. The viral contents was evaluated at passages P.1, P.5, P.10, P.15 and P.20. The results demonstrate that the virus can be replicated in Clon-8 cell monolayers at 34° C. without any loss of viability, at least up to passage P.20 (Table II).

TABLE II

Evolution of the virus propagated in Clon-8 at 34° C. from passage P.1 to passage P.20.

| PASSAGE IN CLON-8 | VIRAL CONTENT IN $TCID_{50}/ml$ |
|---|---|
| P. 1 | $10^{5.5}$ |
| P. 5 | $10^{5.7}$ |
| P. 10 | $10^{5.5}$ |
| P. 15 | $10^{5.6}$ |
| P. 20 | $10^{6.2}$ |

Further results confirmed that Clon-8 cell monolayers could be infected at a MOI of 0.001.

Trials performed as described in the next example showed that the P.20 derived viral strain was innocuous to swine.

Example 4

Biological Characterization of the Attenuated Viral Strain and Effects of the Vaccination with the Same The starting viral strain used to obtain the attenuated strain object of the invention is a virulent strain. The main effects on pregnant sows are premature parturitions and weak, death and/or mummified newborn piglets. The infected sows also show depression and a 3–5 day period of slight anorexia at 4–5 days post-infection.

Four pregnant sows (references 01, 02, 03 and 06) were infected by intranasal route with $10^{6.6}$ $TCID_{50}$ of the starting virulent strain. Two uninfected sows (references 73 and 74) were used as a control. The results are shown in table III.

TABLE III

Effects on the offspring of pregnant sows inoculated with virulent virus.

| SOW REFERENCE | VIRULENT VIRUS INOCULATION | NUMBER OF BORN PIGLETS | | | NUMBER OF DEAD PIGLETS UNTIL WEANING |
|---|---|---|---|---|---|
| | | LIVE | DEAD | MUMMIFIED | |
| 01 | + | 10 | 2 | 0 | 2 |
| 02 | + | 15 | 0 | 0 | 4 |
| 03 | + | 6 | 5 | 0 | 2 |
| 06 | + | 6 | 6 | 0 | 1 |
| 73 | − | 13 | 0 | 0 | 0 |
| 74 | − | 10 | 0

Only one infected sow farrowed at the expected date. The infected sows farrowed 2, 0, 5 and 6 stillborn piglets and 2, 4, 2 and 1 weak piglets, respectively. The weak piglets died a few days after birth. At weaning, an average of 11 piglets from each control sow were alive. Only an average of 6.5 piglets from each infected sow were alive when weaned. At weaning, the mean weight of the piglets was 4,621 g (piglets from infected sows) and 5,365 g (piglets from control sows). Virulent PRRS virus was isolated from homogenized lungs of weak-born piglets. After the challenge infection, both infected sows and their offspring seroconverted.

Figure 2:
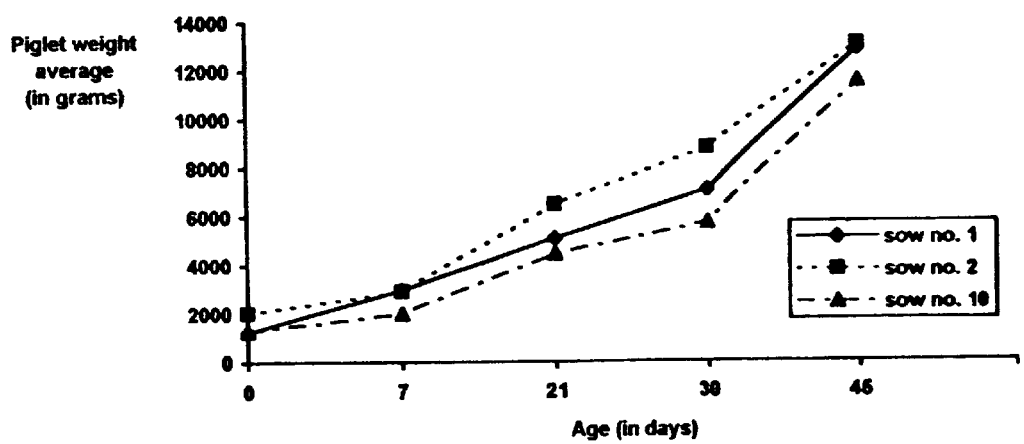
FIG. 2 shows a two-dimension figure representing the weight evolution of piglets born of sows inoculated with the attenuated strain object of the present invention.

The biological characterization of the attenuated viral strain object of the invention was carried out, depending on the specific test, using pigs of both sexes. The innocuousness test was performed in 3 PRRS seronegative pregnant sows from a small farm where PRRS outbreaks had never been detected. The sows were inoculated in the last third of pregnancy, when the sensitivity to the virus is maximum. A dosage of $10^6$ $TCID_{50}$/sow of the attenuated virus was administered by intranasal route between days 78th and 93rd of pregnancy. After the virus inoculation, the physiological constants of the three sows remained unchanged and the rectal temperature was within the normal parameters (see FIG. 1). The three sows also farrowed at the expected date. The results obtained are summarized in table IV.

all cases (see FIG. 2) and it was within the normal parameters until the end of the observation period (45 days). Symptoms of weakness and disorders which could be related with PRRS virus infection were not found in any piglet. Additionally, PRRS virus was detected neither in blood nor in serum samples from the newborn piglets.

Figure 3:
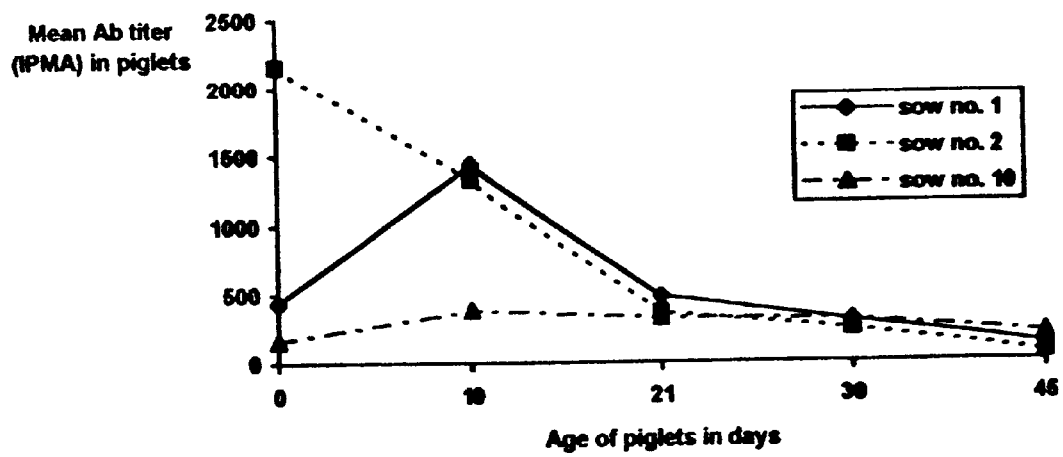
FIG. 3 shows a two-dimension figure representing the colostral antibody kinetics as determined by IPMA, in the offspring of sows vaccinated with the attenuated strain object of the present invention. The lower titers in the offspring of sows 1 and 10 at birth are due to the fact that some piglets had not already sucked the colostrum at the moment the blood was drawn.

Neither was PRRS virus detected in blood and serum samples from pregnant sows at 21–36 days after the virus inoculation. All these facts prove the innocuousness of the attenuated PRRS strain in pregnant sows which are, precisely, the most susceptible category to the infection with wild type virus. All serum samples from the newborn piglets from inoculated pregnant sows were found to be negative when screened for the presence of PRRS virus in PAM cultures by using conventional techniques. The three sows inoculated with the attenuated virus had humoral antibodies with IPMA titers of 1/480 at 45 days after farrowing, being stable with little deviations from that day. Sows were found to be seropositive as soon as 21 days after the inoculation. As can be seen in FIG. 3, piglets from inoculated sows were found seropositive after sucking the colostrum and remained seropositive, at least, until 75 days old.

A further innocuousness test was performed in a group of 12 pregnant sows in the last third of pregnancy. Eight sows were vaccinated intramuscularly with 39 vaccine doses ($10^5$ $TCID_{50}$) and the remaining four sows were used as controls to evaluate the effects of the attenuated strain on the repro-

TABLE IV

Effects on the progeny of pregnant sows inoculated with the attenuated virus.

| SOW REFERENCE | ATTENUATED VIRUS INOCULATION | NUMBER OF BORN PIGLETS | | | NUMBER OF DEATHS CAUSED BY PRRS UNTIL WEANING |
|---|---|---|---|---|---|
| | | LIVE | DEAD | MUMMIFIED | |
| 1 | + | 13 | 0 | 3 | 0 |
| 2 | + | 4 | 1 | 0 | 0 |
| 10 | + | 16 | 0 | 1 | 0 |

The three sows gave rise to 13, 4 and 16 piglets respectively. The vitality of newborn piglets was considered as normal. However, several mummified piglets were found in the progeny of two sows. This can be considered as normal taking into account the large litters from these sows. The weight evolution of the piglets was considered as normal in ductive parameters. No changes were observed in the physiological parameters of the vaccinated sows which farrowed at the expected date. Results are shown in table V. As can be observed in this table, both the eight inoculated sows and the four control sows farrowed a normal number of piglets. Piglets also had a normal viability.

TABLE V

Effects of the inoculation of the attenuated virus on the reproductive parameters of pregnant sows in the last third of pregnancy.

| Reference of the sow | Vaccinated | Deviation from the expected farrowing date (in days) | No. of live piglets (A) | No. of piglets weighing less than the group weight average (B) | No. of weak-born piglets (C) | No. of stillborn piglets (D) | No. of mummified piglets (E) | Total number of piglets (F) |
|---|---|---|---|---|---|---|---|---|
| 86 | yes | 1(+) | 11 | 1 | 0 | 1 | 0 | 12 |
| 94 | yes | 0 | 9 | 0 | 0 | 0 | 1 | 10 |
| 96 | yes | 1(+) | 13 | 2 | 1 | 0 | 0 | 13 |
| 102 | yes | 2(+) | 13 | 1 | 0 | 1 | 2 | 16 |
| 116 | yes | 0 | 10 | 0 | 0 | 1 | 0 | 11 |
| 121 | yes | 1(+) | 11 | 0 | 0 | 1 | 0 | 12 |
| 143 | yes | 1(−) | 14 | 2 | 1 | 2 | 1 | 17 |

TABLE V-continued

Effects of the inoculation of the attenuated virus on the reproductive parameters of pregnant sows in the last third of pregnancy.

| Reference of the sow | Vaccinated | Deviation from the expected farrowing date (in days) | No. of live piglets (A) | No. of piglets weighing less than the group weight average (B) | No. of weak-born piglets (C) | No. of stillborn piglets (D) | No. of mummified piglets (E) | Total number of piglets (F) |
|---|---|---|---|---|---|---|---|---|
| 151 | yes | 2(+) | 8 | 0 | 0 | 0 | 0 | 8 |
| 76 | no | 2(+) | 7 | 0 | 0 | 0 | 2 | 9 |
| 79 | no | 0 | 13 | 2 | 1 | 1 | 0 | 14 |
| 81 | no | 1(−) | 9 | 0 | 1 | 0 | 0 | 9 |
| 83 | no | 1(−) | 10 | 1 | 0 | 1 | 1 | 12 |

A includes B and C
F = A + D + E

Figure 4:
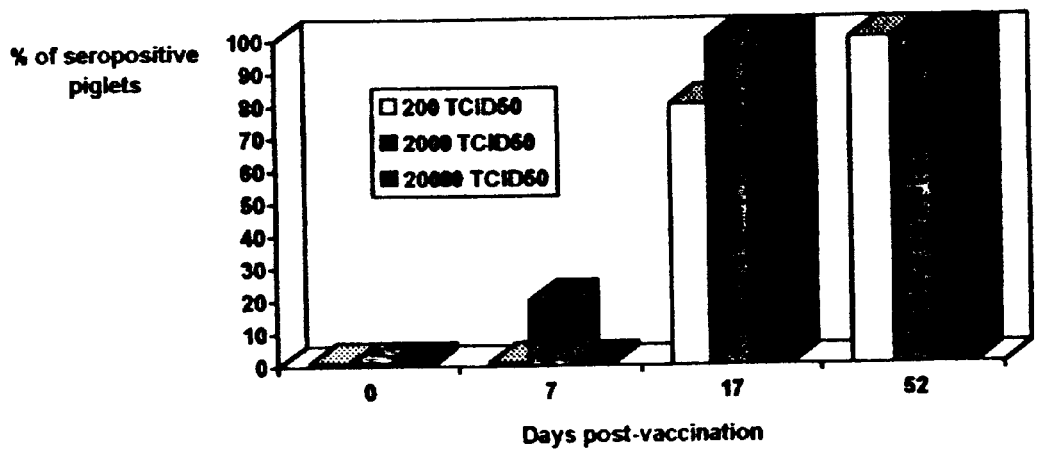
FIG. 4 shows a three-dimension figure representing the humoral response evolution in piglets inoculated by intramuscular route with 200, 2,000 and 20,000 TCID$_{50}$ of the attenuated strain object of the present invention.

The attenuated virus object of the present invention replicates efficiently in PRRS-seronegative pigs. This is demonstrated by the fact that as little as 200 $TCID_{50}$ administered intramuscularly can replicate and induce seroconversion in pigs. As can be seen in FIG. 4, the antibodies induced persist for at least 52 days in the inoculated animals.

The attenuated virus object of the present invention does not spread to four non-inoculated sentinel piglets placed together with a group of eight intramuscularly inoculated piglets. The fact that virus is not transmitted to non-vaccinated animals illustrates the suitability of the attenuated strain as a vaccine. Moreover, no leukopenia or any other clinical sign is observed in vaccinated pigs, showing that the attenuated virus is also innocuous when administered intramuscularly. An average of 86% of inoculated piglets became seropositive as soon as 11 days after the inoculation.

The attenuated virus object of the present invention induces a protective immune response in vaccinated pigs that prevents the clinical effects of an challenge infection with the virulent PRRS strain. Thus, no clinical symptoms were observed in 75% of four week old vaccinated piglets when they were infected with the virulent virus. On the other hand, as can be seen in table VI, 80% of unvaccinated control piglets underwent a significant rectal temperature increase after the experimental infection. Furthermore, in a necropsy performed 19 days after the experimental infection, the vaccinated piglets showed significantly less lung lesions than control unvaccinated piglets. In the same way, after the experimental infection virulent virus was found only in 25% of vaccinated animals, whereas virulent virus could be detected up to at least 12 days post-infection in 80% of unvaccinated control animals.

TABLE VI

Hyperthermia in both vaccinated and control piglets after the challenge infection

| | No. of piglets showing hyperthermia/ total no. of piglets | No. of days with hyperthermia |
|---|---|---|
| Vaccinated piglets (intramuscular route) | 1/4 | 1 |
| Unvaccinated piglets | 4/5 | 8 |

INFORMATION ON THE DEPOSITED MICROORGANISMS

According to the Budapest Treaty, both the viral strain and the cell Clon-8 object of this invention were deposited in the International Authority of the Collection Nationale de Cultures de Microorganismes (CNCM) of the Institut Pasteur, Paris (France)

| Applicant Identification | CNCM Number | Deposit Date |
|---|---|---|
| VP-046-BIS | I-1642 | 23/11/95 |
| Clon-8 | I-1643 | 23/11/95 |

These deposits are at public disposal under the conditions specified in the Budapest Treaty. This cannot be interpreted as a license to put into practice the object of the present invention thus infringing the rights of the applicant of the present patent.

We claim:

1. A vaccine to protect swine against the disease known as porcine reproductive and respiratory syndrome (PRRS) containing the attenuated viral strain that corresponds to the deposit on Nov. 11, 1995 with CNCM of Institute Pasteur, having access number I-1642.

2. A vaccine according to claim 1 characterized by containing between $10^2$ and $10^6$ $TCID_{50}$ of the attenuated viral strain.

3. A vaccine according to claim 1, wherein the vaccine dose contains the attenuated viral strain or inactivate virus.

4. A vaccine according to claim 1, containing additional immunostimulating adjuvants and/or emulsifiers and/or stabilizers.

5. A vaccine according to claim 1, containing additional swine viruses either live or inactivated, in either single or combined form.

6. A vaccine according to claim 1 containing additional live or inactivated bacteria.

* * * * *